United States Patent [19]

Hardwick

[11] Patent Number: 5,103,790
[45] Date of Patent: Apr. 14, 1992

[54] CHEMICALLY HEATED BLANKET

[75] Inventor: E. Russell Hardwick, Encino, Calif.

[73] Assignee: Karen Worchell, Studio City, Calif.

[21] Appl. No.: 433,697

[22] Filed: Nov. 9, 1989

[51] Int. Cl.⁵ ............................................. F24J 1/00
[52] U.S. Cl. .................................... 126/263; 126/204; 128/403
[58] Field of Search .............. 126/263, 204, 205, 206, 126/400, 907, 269; 128/254, 403, 399, 402; 165/46

[56] References Cited

U.S. PATENT DOCUMENTS

| | | | |
|---|---|---|---|
| 4,516,564 | 5/1985 | Koiso et al. | 126/204 |
| 4,572,188 | 2/1986 | Augustine et al. | 126/204 |
| 4,664,674 | 5/1987 | Oftedal et al. | 126/263 |
| 4,756,299 | 7/1988 | Podella | 126/204 |

*Primary Examiner*—James C. Yeung
*Attorney, Agent, or Firm*—Irell & Manella

[57] ABSTRACT

The present invention relates to a chemical warmer which comprises an air supply device, a first and a second panel peripherally fastened to each other to form an envelope to contain a chemical thermogenic material. The first panel is configured to include an air-impermeable top layer, an air-permeable middle layer with a plurality of air holes therethrough and an air-permeable inner layer with many micropores therethrough, the top and middle layers being partially welded to each other in such a way that a plurality of air distribution passages and gas exhaust passages are formed for uniformly distributing air inside the panel and extracting exhaust gases/air to a gas exit which is connected to a size-adjustable wastegate device. The second panel is air-impermeable. The air supply device is either hand-operated or electronically powered.

28 Claims, 2 Drawing Sheets

CHEMICALLY HEATED BLANKET

BACKGROUND OF THE INVENTION

The present invention relates to a chemical warmer, and especially to a chemically heated blanket.

A chemical warmer has many known advantages and uses since no flame is produced. It is widely used in hospitals, homes and outdoors for applying heat to a human body or other objects. Consequently, various types of such devices are known in the art. Many improvements have been made in the chemical exothermic materials used in the chemical warmers, one useful type uses air for activating and maintaining the thermogenic chemical reactions in the chemical warmer. In order to introduce air into a chemical warmer, the conventional chemical warmers usually utilize an air-permeable inner bag which is enclosed in an air-impermeable outer bag, or covered by an air-impermeable film or the like. The inner bag may have one or more air-impermeable layers which are provided with many air holes or micropores. Initiation of the heating process occurs when the inner bag is exposed to air. Numerous patents have been granted for improvements in such chemical warmers such as the following U.S. patents: U.S. Pat. No. 4,756,299 issued on July 12, 1988 to Car W. Podella, U.S. Pat. No. 4,268,272 issued on May 19, 1981 to Miyako Taura, U.S. Pat. No. 3,976,049 issued on Aug. 24, 1976 to Iwao Yamashita et al, and U.S. Pat. No. 3,301,250 issued on Jan. 31, 1967 to Ernest C. Glasser.

One of the important factors which affects the thermogenic reaction is the amount of air supply per time unit. Due to the structures of the previous chemical warmers, the rate of air supply is adjustable only to a very imprecise degree. As a result, the heat output from the warmer cannot be effectively controlled. In other words, the temperature of the chemical warmer is not controllable. Moreover, in most prior art, the air cannot be efficiently and uniformly supplied to all parts of the thermogenic material, causing hot and cold spots. Furthermore, the thermogenic reaction or heating process is not easily stopped when desired as to the prior art. Normally, the conventional chemical warmer must be taken away from the heated body and put back into an air-impermeable bag or resealed by a film in order to stop the production of heat.

All of these shortcomings associated with the conventional chemical warmers limit their applications or areas of use.

The present invention provides a novel chemical warmer which overcomes the limitations and shortcomings of the prior art devices.

OBJECT OF THE INVENTION

One object of the present invention is to provide a chemical warmer which can control the heat output of the chemical warmer by controlling the supply of air.

Another object of the present invention is to provide a chemical warmer that can efficiently and uniformly distribute air to all parts of the warmer.

Still another object of the present invention is to provide a chemical warmer in which the production of heat can be easily stopped without removing the chemical warmer from the context of its application.

A further object of the present invention is to provide a chemically heated blanket that has the above-mentioned advantages and can be used in hospitals, homes, automobiles or outdoors.

These and other important objects of the present invention will be apparent from the detailed description provided hereafter.

SUMMARY OF THE INVENTION

This invention is an improved chemical warmer or chemically heated blanket of the air-activated type, which can supply heat to the human body or other objects. The chemically heated blanket comprises an air supply device for introducing atmospheric air into the blanket, a gas exhaust exit for extracting the exhaustion gases, and first and second panels forming an envelope which contains the chemical exothermic material.

The first panel, functioning as an air distribution and gas exhaust system, includes a top layer of air-impermeable material, a middle layer of air-permeable material with a plurality of air holes therethrough and an inner layer of air-permeable material having many air micropores, the top and middle layers being partly welded to each other in such a way that a plurality of air passages and gas exhaust passages are formed between them for uniformly distributing air from the air supply device to inside the panel and transferring exhaust gases to the gas exhaust exit. The second panel is provided with at least a layer of air-impermeable material. The air supply device which is connected to the air passages by means of an air entrance, can be either a hand-operated, an electrically powered type, or any other means of introducing air. The gas exhaust exit is provided with a wastegate, the size of which is adjustable.

In another embodiment, the air distribution system and the gas exhaust system are separately structured on the first and second panels.

Some preferred embodiments and features of the present invention will be described hereafter by referring to the attached drawings.

DETAILED DESCRIPTION OF THE INVENTION

Figure 1:
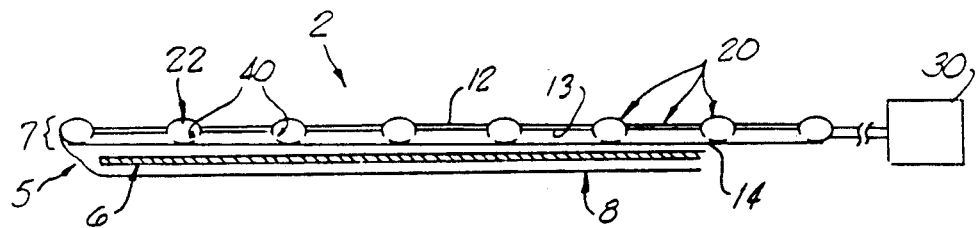
FIG. 1 is a cross-sectional view of an embodiment of the chemically heated blanket of the present invention.
Figure 2:
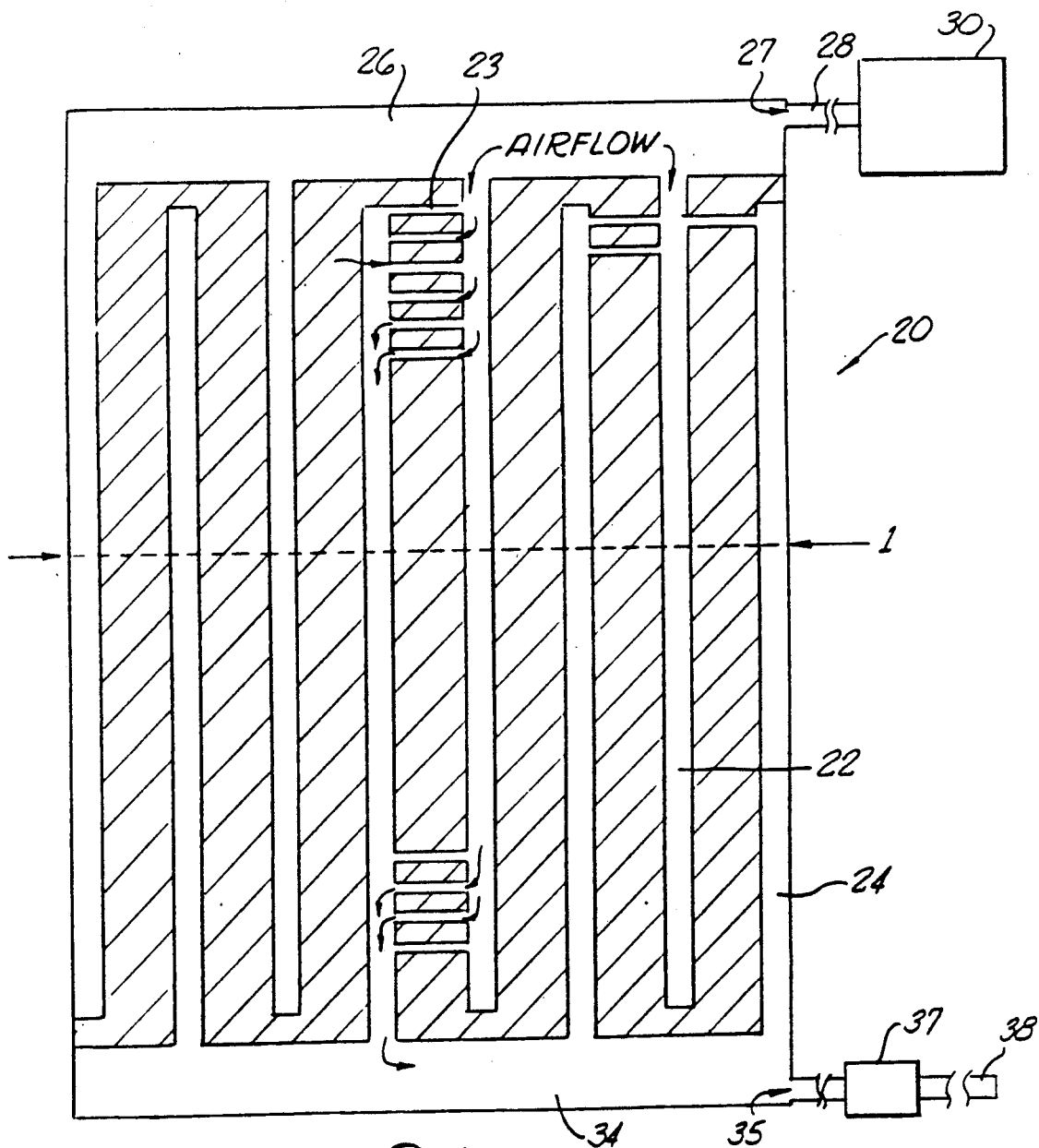
FIG. 2 is a cross-sectional plan view of an arrangement of the air passages and gas exhaust passages of the embodiment shown in FIG. 1.

Turning in detail to the drawings, FIGS. 1 and 2 show a preferred embodiment of a chemically heated blanket 2 of the present invention which has an air supply device 30 and an air distribution and gas exhaust system 20.

The thermogenic chemical material used in the present invention can be any kind of air-oxidizable thermogenic materials known in the prior art, such as the materials described in U.S. Pat. No. 4,093,424.

The chemically heated blanket 2 includes an envelope 5 which is formed by two panels 7 and 8, whereby the exothermic chemical material 6 is accommodated therein. The panel 8 is constructed from a layer of air-impermeable material. The other panel 7 has a laminated configuration which preferably consists of an air-impermeable top layer 12, an air-permeable middle layer 13 with a plurality of air holes 40 therethrough. As an example, these air holes 40 may be 1 mm diameter holes spaced on 1 cm centers, although the size and spacing of the holes will depend on the type of thermogenic material and the intended conditions of use. And an air-permeable inner layer 14 having many micropores therethrough or made of an air-permeable material. The top layer 12 and the middle layer 13 are partially united to each other in such a way that a plurality of air passages and gas exhaust passages are provided. Gas exhaust, as used herein, refers to air exiting from the distribution system together with by-products (to the extent they exist) from the thermogenic chemical reaction. The two panels can be made of thermoplastic materials, heat-welded into the desired form and then incorporated into the blanket.

The arrangement of the passages is shown in FIG. 2, and includes a plurality of longitudinal air passages 22 and longitudinal gas exhaust passages 24, and many transverse sub-passages 23 uniformly arranged between the longitudinal air passages 22 and the longitudinal gas exhaust passages 24 at equal intervals to each other. (Only a few of the transverse sub-passages are schematically shown in FIG. 2.) It should be understood that the arrangement of the passages shown in FIG. 2 is only an example. Some other arrangements may also be chosen as long as the air distribution and gas exhaust system can introduce fresh air and extract exhausted gases uniformly across all parts of the blanket. All the longitudinal air passages are connected to an air entrance chamber 26 extending across the head of the blanket like a section of an air mattress and acting as a buffer against pulsing of the air supply. The entrance chamber 26 can store one or more minutes of air supply and forms the initial distribution mechanism, while all the longitudinal gas exhaust passages are connected to an outlet chamber 34 extending across the opposite head of the blanket with a diameter somewhat smaller than the entrance chamber.

Air is supplied externally through a tube 28 leading to an air entrance 27 of the air entrance chamber 26. Air supply to the tube 28 is from an air supply device 30 which can be a small air compressor or air pump powered by line current, batteries or other means. A small compressor may be incorporated into the blanket itself, with electric power supplied by batteries. Various types of compressors can be used for this purpose, for example, the piston type, diaphragm type, gear type or any device that can deliver air at a suitable pressure. Air may also be delivered by means of a hand-operated air supply device, such as a squeeze bulb, a bellows, an accordion device or other similar means. The air pressure is in range of about 5 to 15 cm of mercury at a rate of 1 or more liters/minute. But it should be understood that the air pressure of the air supply is determined depending on the size of the blanket, the type of thermogenic material used and the temperature needed. It is calculated that an air flow of 1 L/min would be sufficient, given standard thermogenics, to produce a heat in excess of that given by a standard electrically heated twin-bed blanket operated at a moderate rate at temperatures somewhat below room temperature.

The exhaust gases exit from a gas exit 35 leading from the outlet chamber 34. There is provided a wastegate device 37 which is connected to the exit 35 and includes a restricted gate of either fixed or adjustable size for the purpose of assuring an optimum pressure in the blanket system. The wastegate device can be any suitable valve or the like, including a simple cam roller acting in combination with a deformable plastic tube. An outflow tube 38 can be provided for leading the exhaust gases away from the blanket to diminish the concentration of exhaust gases near the person lying on the blanket.

During the thermogenic operation, air is supplied by means of the air supply device 30 into the air entrance chamber 26, then air is delivered into a series of air passages 22 under pressure so that second stage of air distribution occurs. Air continues flowing into subpassages 23 in a matrix pattern and final air distribution occurs. Passing through the holes on the layer 13 of the air distribution system, air reaches the final air-permeable layer 14 in a uniform manner. Finally, air passes through the final layer 14 and activates the thermogenic reaction. Any gases produced in the reaction together with excess air will exit through the gas exhaust passages 24 under the difference in pressures between the gas exhaust system and reaction space. Control of the heat output of the blanket is simply by controlling the rate of input airflow. If the airflow is stopped completely, the blanket could be shut off by terminating the air necessary to react with the thermogenic materials.

Figure 3:
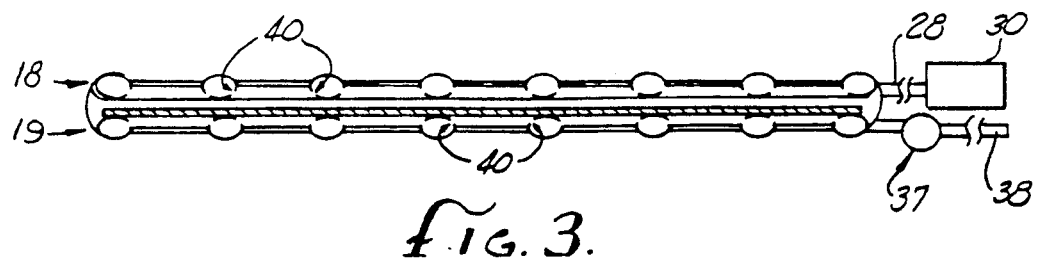
FIG. 3 is a cross-sectional view of another embodiment of the chemically heated blanket of the present invention.
Figure 4:
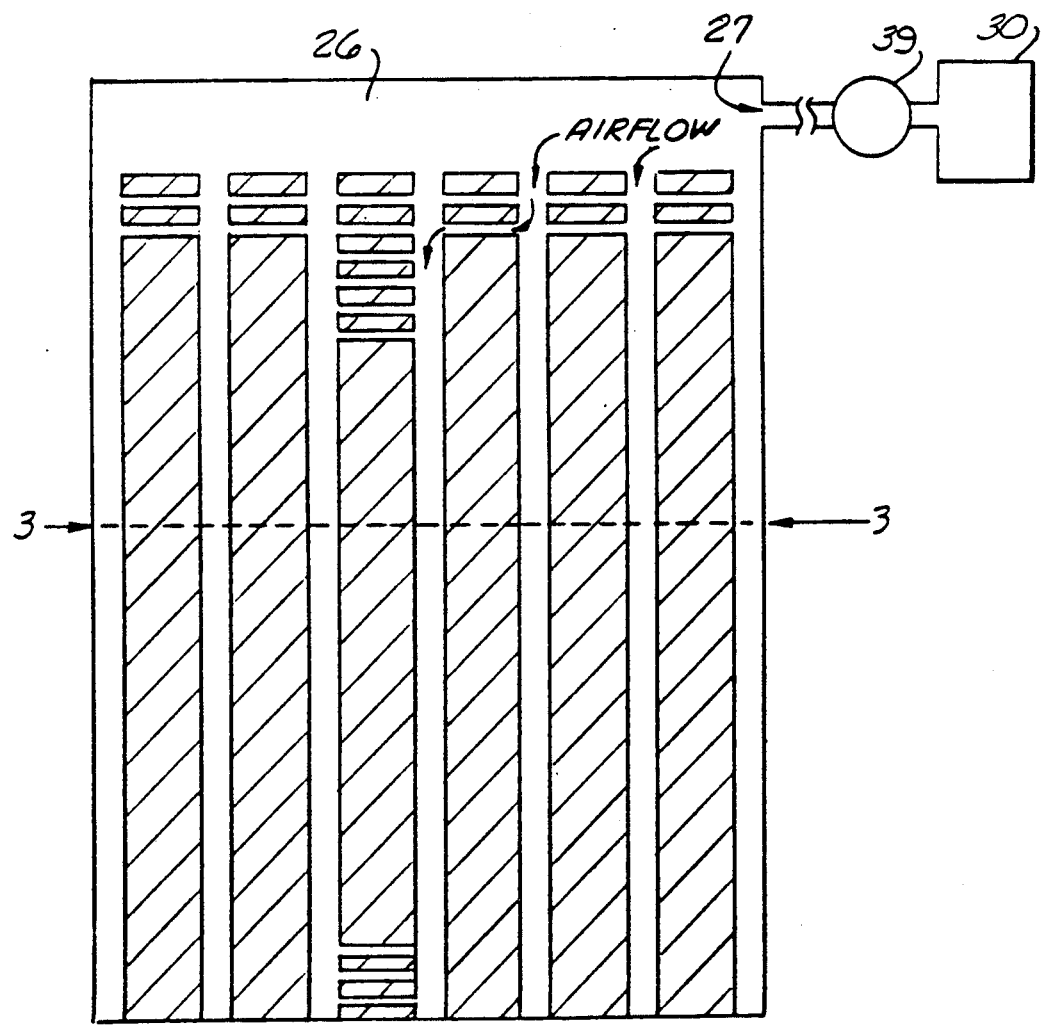
FIG. 4 is a cross-sectional plan view of the arrangement of the air passages of the embodiment shown in FIG. 3.

Referring now to FIGS. 3 and 4, there is shown another embodiment of the chemically heated blanket which has an air distribution system 18 on one panel of the blanket, and a similarly structured gas/air exhaust system 19 on the other panel. The outlet chamber, in this case, can be at the same end as the entrance chamber 26, allowing better access to wastegate control. In use, the exhaust surface may be the surface next to the human body so as to help distribute heat evenly, diminishing the presence or effect of hot spots. In this embodiment, it is necessary that air be able to pass through the thermogenic material, which can be configured to make this possible.

In order to obtain a calibrated heat output, particularly when the blanket is used in hospitals, an air flowmeter 39 or a pressure gauge may be employed on the air input line or on the gas output line.

While the preferred application of the present invention has been shown and described, it should be apparent to those skilled in the art that many more modifications are possible without departing from the invention concept herein described. It is intended to cover in the appended claims all such modifications as fall within the true spirit and scope of the invention.

What is claimed is:

1. A chemical warmer which can directly warm up an object or a person, comprising:
    a thermogenic material,
    a first sheet of air-impermeable material and a second sheet of air-impermeable material pheripherally connected to said first sheet to form an air-impermeable envelope for containing said chemical thermogenic material, said first and second sheets of air-impermeable material having inner and outer surfaces,
    an air distribution means for distributing air into said air-impermeable envelope, said air distribution means being arranged between said thermogenic material and said air-impermeable envelope, and being connected to an air entrance on said envelope,
    a gas exhaust means for exhausting exhaust gas out of said air-impermeable envelope, said gas exhaust means being arranged between said thermogenic material and said air-impermeable envelope and being connected to a gas exit on said envelope,
an air supply means separably connected to said air entrance for supplying air into said air distribution system.

2. A chemical warmer claimed in claim 1, wherein said air distribution means and said gas exhaust means are formed in such a way that a first sheet of air-permeable material with a plurality of air holes therethrough is partially united to the inner surfaces of said first or second sheet of air-impermeable material so that a plurality of air distribution passages and gas exhaust passages are provided.

3. A chemical warmer claimed in claim 2, wherein said air distribution means and gas exhaust means further includes a second sheet of air-permeable material with a plurality of micropores therethrough which is disposed between said thermogenic material and said first sheet of air-permeable material, and peripherally connected to said first sheet of air-permeable material.

4. A chemical warmer claimed in claim 1, wherein said air supply means includes an air injection means for injecting air into said air distribution means under pressure.

5. A chemical warmer claimed in claim 4, wherein said air injection means is either of a hand-operated type or electrically powered type.

6. A chemical warmer claimed in claim 1, wherein said air supply means further includes an air flowmeter or a pressure gauge for controlling the rate of airflow so as to control the heat output of said warmer.

7. A chemical warmer claimed in claim 1, further including a means for controlling the rate of gas output.

8. A chemical warmer claimed in claim 1 or 7, including a tube for leading exhaust gases away from said chemical warmer.

9. A chemical warmer, comprising:
an external air supply means for supplying air into a first panel means,
a first panel means including at least one sheet of air-impermeable material and at least one sheet of air-permeable material with a plurality of air holes therethrough, said two sheets being partially connected in such a way that a plurality of air passages are provided for uniformly distributing air to inside said first panel means,
a second panel means peripherally connected to said first panel means to form an envelope, and including at least one sheet of air-impermeable material and at least one sheet of air-impermeable material with a plurality of air holes therethrough, said two sheets being partially connected in such a way that a plurality of gas passages are provided for extracting exhaust gases, and
a chemical exothermic composition disposed in said envelope.

10. A chemical warmer claimed in claim 9, wherein said air supply means includes an air injection means for injecting air into said first panel means under pressure.

11. A chemical warmer claimed in claim 10, wherein said air injection means is hand-operated or electrically powered.

12. A chemical warmer claimed in claim 10 or 11, wherein said air supply means further includes an air flow meter or a pressure gauge and an inlet valve means for controlling the rate of airflow so as to control the heat output of said blanket.

13. A chemical warmer claimed in claim 9, further includes a gas exhaust means which has an outlet valve means for controlling the rate of output airflow to assure an optimum pressure in said blanket.

14. A chemical warmer claimed in claim 9 or 13, wherein said gas exhaust means further includes a pipe means for leading exhausted gases away from said blanket.

15. A chemical warmer claimed in claim 9, wherein said first panel further includes an air-permeable sheet adjacent to said exothermic composition.

16. A chemically heated blanket comprising:
an air injection means for introducing air into a first panel means under pressure,
a gas exhaust means for extracting exhaust gases,
a first panel including a top sheet of air-impermeable material, a middle sheet of air-permeable material with a plurality of air holes therethrough and a bottom sheet of air-permeable material with many air micropores therethrough, said top and middle sheets being partially welded to each other in such a way that a plurality of air passages and gas exhaust passages are provided for uniformly distributing air to inside the first panel and transferring exhaust gases to said gas exhaust means,
a second panel peripherally fastened to said first panel to form an envelope and including at least one sheet of air-impermeable material, and
a chemical exothermic composition disposed in said envelope.

17. A chemically heated blanket claimed in claim 16, wherein said air passages include a transverse entrance chamber having an air entrance acting as a buffer against pulsing of the air supply from said air injection means, a plurality of longitudinal passages and a plurality of transverse sub-passages coupled to said longitudinal passages.

18. A chemically heated blanket claimed in claim 17, wherein said transverse sub-passages have a smaller diameter than said longitudinal passages.

19. A chemically heated blanket claimed in claim 16, wherein said gas exhaust passages include a plurality of longitudinal passages and a transverse outlet chamber having a gas exit.

20. A chemically heated blanket claimed in claim 17 or 19, wherein said transverse sub-passages are connected to said gas exhaust longitudinal passages.

21. A chemically heated blanket claimed in claim 16, wherein the rate of airflow output of said air injection means can be controlled.

22. A chemically heated blanket claimed in claim 16 or 21, further includes an air flowmeter.

23. A chemically heated blanket claimed in claim 16 or 21, further includes an inlet valve means for controlling the rate of airflow so as to control the temperature of said blanket.

24. A chemically heated blanket claimed in claim 16, wherein said air injection means is hand-operated or electrically powered.

25. A chemically heated blanket claimed in claim 16, wherein said gas exhaust means includes an outlet valve means for controlling the amount of airflow output.

26. A chemically heated blanket claimed in claim 16 or 25, wherein said gas exhaust means further includes a pressure gauge.

27. A chemically heated blanket claimed in claim 16, wherein said gas exhaust means includes a pipe means for leading exhausted gases away from said blanket.

28. A chemically heated blanket claimed in claim 16, wherein said first panel further includes a sheet of air-permeable material adjacent to said exothermic composition.

* * * * *